(12) United States Patent
Burman et al.

(10) Patent No.: US 7,699,987 B2
(45) Date of Patent: Apr. 20, 2010

(54) STABILIZED FORMULATION

(75) Inventors: Anand C. Burman, Ghaziabad (IN); Rama Mukherjee, Ghaziabad (IN); Dinesh Kumar, Ghaziabad (IN); Dhiraj Khattar, Ghaziabad (IN); Mukesh Kumar, Ghaziabad (IN); Praveen Khullar, Ghaziabad (IN); Perundurai S. Srinivasan, Ghaziabad (IN); Rajesh Srivastava, Ghaziabad (IN)

(73) Assignee: Dabur Pharma Ltd., New Delhi (IN)

(*) Notice: Subject to any disclaimer, the term of this patent is extended or adjusted under 35 U.S.C. 154(b) by 986 days.

(21) Appl. No.: 11/449,476

(22) Filed: Jun. 8, 2006

(65) Prior Publication Data

US 2006/0226076 A1 Oct. 12, 2006

Related U.S. Application Data

(62) Division of application No. 10/626,501, filed on Jul. 24, 2003, now abandoned.

(51) Int. Cl.
*B01D 15/08* (2006.01)
(52) U.S. Cl. ............... 210/635; 210/656; 210/198.2
(58) Field of Classification Search ............ 514/449; 554/219; 210/635, 656, 198.2
See application file for complete search history.

(56) References Cited

U.S. PATENT DOCUMENTS

| 5,504,102 | A | 4/1996 | Agharkar et al. |
| 5,925,776 | A | 7/1999 | Nikolayev et al. |
| 6,071,952 | A | 6/2000 | Owens et al. |
| 6,153,644 | A | 11/2000 | Owens et al. |
| 6,306,894 | B1 | 10/2001 | Carver et al. |
| 6,388,112 | B1 | 5/2002 | Anevski |
| 6,710,195 | B2 | 3/2004 | Jodhi-Hangal et al. |
| 2005/0016926 | A1* | 1/2005 | Burman et al. ............ 210/656 |
| 2006/0058541 | A1* | 3/2006 | Zhang et al. ............. 554/191 |

FOREIGN PATENT DOCUMENTS

| WO | 98/57630 | 12/1998 |
| WO | 00/23070 | 4/2000 |
| WO | 01/52838 | 7/2001 |

OTHER PUBLICATIONS

South African Application No. 984,832, an English Equivalent of WO 98/57630, Apr. 1998.*

* cited by examiner

*Primary Examiner*—Ernest G Therkorn
(74) *Attorney, Agent, or Firm*—Ladas & Parry LLP

(57) ABSTRACT

A stabilized pharmaceutical composition of anticancer drug and a solvent like Polyethoxylated castor oil (cremophor) also containing any other suitable solubilizer suitable for human administration like dehydrated alcohol, is disclosed. Compositions prepared using this purified polyethoxylated castor oil enhance the stability of paclitaxel in such compositions.

18 Claims, No Drawings

STABILIZED FORMULATION

This application is a divisional of application number 10/626,501 filed on Jul. 24, 2003 now abandoned, claims the benefit thereof and incorporates the same by reference.

The present invention relates to a stabilized pharmaceutical composition in a solvent system and in particular a co-solvent system suitable for preparing a stabilized injection composition containing at least one pharmaceutical agent. More particularly, the present invention relates to stabilized compositions of anti cancer drugs.

Administration of pharmaceutical compounds, particularly by injection, usually requires a suitable solvent or delivery system to enable the composition to be administered to a patient.

An ideal solvent must typically have the following properties:

1. It must be capable of solubilizing a therapeutically effective amount of the active agent to produce an effective composition.
2. It must be compatible with the active agent.
3. It should be safe i.e. it should not cause any toxicity to the patient.
4. It should produce a composition having a good shelf life.

Many solvents while possessing most of the above advantageous qualities are not particularly efficient in solubilizing the pharmaceutical agent to produce an effective composition for administration.

On the other hand numerous pharmaceutical agents are not sufficiently soluble in any one solvent to enable the resulting composition to be effective. Therefore, mixtures of two or more solvents are quite commonly used in pharmaceutical industry to overcome the limitations of a single solvent to solubilize the active agent. These co-solvent systems are suitable for solubilizing many pharmaceutical agents, which cannot otherwise be solubilized or dispersed in a single solvent.

One example of a co-solvent system is a mixture of a polar solvent and a non-ionic solvent, such as a mixture of a polyethylene glycol and Cremophor EL or ELP (polyethoxylated castor oil). Cremophor EL or ELP is a condensation product of castor oil and ethylene oxide sold by BASF.

Although these co-solvent systems can be effective in solubilizing many compounds, they are not without their disadvantages. A commonly used co-solvent system used for many pharmaceutical agents is a 50:50 mixture of ethanol and Cremophor ELP. A potential problem associated with such solvents is that acids, salts or other ionic impurities, as well as residual water in the solvent or solvent system, even if within the acceptable limits, can catalyze the degradation of the pharmaceutical agent. For example, co-solvents of ethanol and Cremophor are known to result in particulates forming upon dilution with infusion solutions. In addition, fibrous precipitates of unknown composition form in some formulations during storage for extended periods of time.

A solvent with sufficiently low levels of particularly deleterious impurities will yield more stable pharmaceutical compositions. The US FDA approved pharmaceutical composition of Taxol marketed by Bristol Myers Squibb is paclitaxel in a co-solvent of 50:50 by volume of dehydrated ethanol and commercial grade Cremophor EL. These compositions exhibit a loss of potency of greater than 60% after storage for 12 weeks at 500 C. (U.S. Pat. No. 5,504,102). The loss of potency is attributed to the decomposition of paclitaxel during storage. It is believed that carboxylate anions present in Cremophor EL can catalyze the decomposition of paclitaxel, even at levels within the defined limits set forth in the National Formulary. U.S. Pat. No. 5,504,102 (Agharkar et al) incorporated herein by reference discloses removing the carboxylate anions from polyethoxylated castor oils (cremophor) by acid addition or alumina adsorption. U.S. Pat. No. 5,504,102 discloses that paclitaxel reacts with ethanol during storage and that the decomposition of paclitaxel is catalyzed by the carboxylate anions in the solvent. They also disclose that lowering the carboxylate concentration of the solvent produced a stabilizing effect on the pharmaceutical composition. The composition in question being Taxol, prepared as an injection concentrate containing 6 mg/ml paclitaxel in 50:50 by volume ethanol and polyoxyethylated castor oil.

As per their disclosure, the pharmaceutical agents of interest are those having an ester linkage that can be cleaved by an alcohol in the presence of carboxylate anions. In their preferred embodiments, the solvent is a co-solvent mixture of at least one solvent and a solubilizing agent. The preferred solvent includes alcohol such as dehydrated ethanol. The solubilizing agent in preferred embodiments is a polyoxyethylated castor oil such as that sold under the tradename Cremophor EL or Cremophor ELP by BASF.

In their preferred embodiments, the carboxylate anion content of the solvent is lowered by a number of methods. In one embodiment of the invention, the Cremophor EL or other solvent is passed through a standard chromatography column of aluminum oxide which adsorbs the carboxylate anions as well as other impurities to reduce the carboxylate anion content of the solvent. In an alternative embodiment, the solvent is treated by the addition of an acid in a stabilizing amount to reduce the carboxylate anion content to a sufficiently low level to substantially prevent catalyzed degradation of the pharmaceutical compound.

Nikolayev et al in U.S. Pat. No. 5,925,776 disclose a method of reducing the cation content in the polyethoxylated castor oil (cremophor). This is achieved by pre-treating the polyethoxylated castor oil with a strong cation exchange resin. The low cationic content polyethoxylated castor oil of the invention is then utilized to prepare formulations of various agents which are found to be sensitive to the previously commercially available polyethoxylated castor oil (cremophor EL). The stability of paclitaxel formulated in a mixture of low cationic content polyethoxylated castor oil of the invention and ethyl alcohol is shown to be better as compared to a formulation using untreated polyethoxylated castor oil of the invention and ethyl alcohol.

Anevski et al in U.S. Pat. No. 6,388,112 disclose a process for purifying a non-ionic surfactant or solvent capable of dispersing and solubilizing a pharmaceutical compound. In the process, a solution of solvent and alcohol is brought in contact with an activated carbon column and an ion exchange resin column. The process is particularly adapted to the purification of polyethoxylated castor oils. The purified solvent is useful in the preparation of pharmaceutical compositions having enhanced shelf life, such as for use with paclitaxel.

Carver et al in U.S. Pat. No. 6,306,894 disclose a pharmaceutical formulation of paclitaxel and polyethoxylated castor oil wherein the formulation is relatively acidified to a pH of less than 8.1 and preferably within a pH range of 5 to 7, inclusively. Ethanol is optionally included in the formulation. A formulation method is also disclosed and includes the step of mixing an acid with a carrier material, such as polyethoxylated castor oil, to form a carrier solution after which paclitaxel is added in an amount such that the resulting pH is less than 8.1 and preferably in a pH range of 5 to 7. Ethanol may optionally be slurried with the paclitaxel before mixing with the carrier solution.

A variety of acidifing agents, a preferred one being anhydrous citric acid, are described. Acids in the form of powders, for example citric acid, have been preferred over those which contain water, for example sulfuric acid. The most preferred acid for use in accordance with the invention disclosed in U.S. Pat. No. 6,306,894 is citric acid, but a wide range of acids may be used including:

Citric acid-monohydrous, Citric acid-anhydrous, Citric acid-hydrous, Acetic acid, Formic acid, Ascorbic acid, Aspartic acid, Benzene sulphonic acid, Benzoic acid, Hydrochloric acid, Sulphuric acid, Phosphoric acid, Nitric acid, Tartaric acid, Diatrizoic acid, Glutamic acid, Lactic acid, Maleic acid, and Succinic acid.

Owens et al in U.S. Pat. No. 6,071,952 disclose a pharmaceutical composition with long term storage stability comprising a taxane or taxoid by incorporating an effective amount of an antioxidant.

Previous efforts to develop a shelf stable composition of some pharmaceutical compositions in various co-solvent systems have not been entirely successful. Thus, there is a continuing need in the art for a solvent or co-solvent system capable of being used for preparing stabilized compositions and, in particular, stabilized injection compositions containing a pharmaceutical agent.

The disadvantages and limitations of the previous injection composition and solvent systems are overcome by the present invention while providing a convenient and efficient method of producing a solvent and a method of stabilizing pharmaceutical compositions including compositions suitable for injection. The present invention is primarily directed to a solvent suitable for producing a stabilized pharmaceutical composition and to a method of producing and stabilizing a pharmaceutical composition.

The invention is directed to a solvent suitable for preparing stabilized injection compositions containing at least one pharmaceutical agent. Accordingly, it is a primary aspect of the invention to provide a method of preparing a treated solvent which when used in a composition has a stabilizing effect on the composition and a method of preparing stabilized pharmaceutical compositions using the treated solvent.

The stabilized pharmaceutical compositions produced using the treated solvent of the invention have been shown to have a shelf life greater than the compositions produced from untreated solvent. The solvent system of the invention is particularly suitable for use with pharmaceutical compounds that exhibit decomposition, which is catalyzed by the presence of ionic, metallic and oxidizing impurities. The advantages of the invention are also attained by producing a stabilized pharmaceutical composition comprising at least one antineoplastic compound and a solvent system capable of solubilising the antineoplastic compound, the solvent system comprising a solubilizing amount of an alcohol such as absolute alcohol and a solubilizer such as polyoxyethylated castor oil having been purified to have an impurities content sufficiently low to substantially minimize degradation of the antineoplastic compound.

Of particular interest are the antineoplastic agents such as paclitaxel, teniposide, camptothecin and derivatives thereof.

DETAILED DESCRIPTION OF THE INVENTION

The solvent system of the invention essentially comprises a purified non-ionic solvent The solubilizing agent can be a condensation product of an alkylene oxide and a lipid or fatty acid. The preferred solubilizing agent includes a polyoxyethylated castor oil such as that sold by M/s BASF under the tradename Cremophor EL or Cremophor ELP and an alcohol. The polyoxyethylated castor oil is purified by a process of chromatography to reduce the water soluble ionic, metallic and oxidizing impurities to a sufficiently low concentration to minimize the decomposition of the pharmaceutical agent that is catalyzed by the presence of these impurities. The content of impurities in the polyoxyethylated castor oil is lowered by reverse-phase chromatography using suitable mobile and stationary phases.

Further advantages of the invention are attained by providing a method of stabilizing a pharmaceutical composition containing a pharmaceutical agent such as paclitaxel, teniposide, camptothecin and derivatives thereof, and a solvent containing absolute ethanol and a purified solubilizing agent as described above.

The invention provides a pharmaceutical stable formulation of paclitaxel made using a purified solvent. The process involves purification of a non-ionic solvent such as polyethoxylated castor oil, preferably polyoxy-35-castor oil, more preferably cremophor such as Cremophor EL or Cremophor ELP using reverse-phase chromatography such that the content of ionic, metallic and oxidizing impurities of the cremophor is lowered.

The process for purifying a non-ionic solvent comprising the steps of:
 (a) forming a solution of the non-ionic solvent in alcohol and water, with or without the aid of heating;
 (b) loading this solution on to a chromatography column packed with reverse phase silica
 (c) running the chromatograph using de-ionized water as the mobile phase to purify the solvent;
 (d) running the chromatograph using an eluent to recover the purified solvent; and
 (e) evaporating the residual water and the eluent.

Preferably the de-ionized water is HPLC grade.

The aqueous fractions obtained from running the chromatograph using de-ionized water are not used and may be set aside or discarded.

Preferably, the solvent is selected from polyethoxylated castor oil, polyoxy-35-castor oil, Cremophor EL or Cremophor ELP.

Preferably, the alcohol is selected from methanol, ethanol, butanol, iso-propanol etc; more preferably ethanol and more preferably dehydrated ethanol.

The eluents may be selected from methanol, ethanol, iso-propyl alcohol, acetone, acetonitrile, tetrahydrofuran and other such solvents of similar polarities. The preferred eluent is acetone. Combinations of eluents may be used.

In one embodiment of the invention the mobile phase is run for 1 to 50 minutes, preferably for 20 minutes.

In one of the preferred embodiments of the invention, the polyethoxylated castor oil is purified by loading it on a chromatography column packed with reverse-phase silica, preferably C-8 or C-18 and chromatographed using de-ionized water to remove or lower the concentration of water soluble impurities—both organic and inorganic. The purified polyethoxylated castor oil is then recovered by eluting the column using an eluent, preferably acetone. Preferably the de-ionized water is HPLC grade.

In a preferred embodiment the weight ratio of polyethoxylated castor oil to alcohol is 10:1. In another embodiment of the invention the ratio of polyethoxylated castor oil to alcohol to water is 10:1:33 w/v/v.

The solvent purified by this method can be combined with antineoplastic compound to form a composition. Optionally the compositions of this invention include an alcohol which may be added to the solvent before combining with the antineoplastic agent when the solvent is combined with the antineoplastic agent or after the solvent is combined with the antineoplastic agent. The alcohol may be a dehydrated alcohol. Compositions suitable for parenteral administration such as injection or infusion may be prepared by diluting the compositions with a suitable parenteral fluid prior to parenteral administration, injection or infusion.

The following non-limiting example is intended to demonstrate the preferred embodiment of the invention. One skilled in the art will readily recognize that numerous embodiments of the invention can be practiced to achieve the stabilizing effect.

EXAMPLE —1

This example was carried out to demonstrate the effect of purification of cremophor using reverse phase chromatography on the stability of Paclitaxel formulation.

300 gm of Cremophor ELP (of M/s BASF) was diluted with about 30 ml of absolute ethanol and the mixture was then dissolved in one liter of HPLC grade de-ionized water preheated to 60° C. with stirring to make uniform solution.

This cremophor solution was then loaded on to a chromatography column (15 cm×30 cm) packed with reverse-phase silica, preferably C-8 or C-18, having an average particle size of 30 to 60μ. The system was eluted using de-ionized HPLC grade water as the mobile phase for about 20 minutes to remove or reduce the water-soluble impurities in the cremophor. The eluted aqueous fractions were discarded. The column was then eluted with 100% acetone to recover the purified cremophor. Acetone was completely removed by evaporation under vacuum using rotavapor at 40° C. The so obtained cremophor was further dried under vacuum at elevated temperature of about 55° C. to remove the residual water to obtain purified cremophor.

The purified cremophor so obtained was tested for various impurities including anions and cations. The cation and anion content was measured in the cremophor before and after purification and the results are as below:

paclitaxel and subjected to stress temperature studies to see the effect on formation of degradation products of paclitaxel.

Samples 1 to 3 were prepared by dissolving 6 mg/ml of paclitaxel in 50:50 v/v mixture of purified cremophor ELP and absolute ethanol. The Cremophor ELP of the samples 1 to 3 was purified as discussed above. Sample 4 was prepared as a control sample from unprocessed Cremophor ELP in a 50:50 v/v mixture of unprocessed Cremophor ELP and ethanol with paclitaxel in the amount of 6 mg/ml.

The samples were then subjected to a stress temperature study at 50° C. The results obtained are summarized as below:

TABLE 1

| Paclitaxel Degradation Products % at 50° C. | | | | |
|---|---|---|---|---|
| PH | | Total (including other degradation products) | | |
| (1:10 dilution in water) | | 3 | 10 | 30 |
| Cremophor | Formulation | Days | Days | Days |
| Sample 1 | 5.02 | 5.04 | 0.07 | 0.14 | 0.24 |
| Sample 2 | 5.03 | 5.08 | 0.09 | 0.16 | 0.28 |
| Sample 3 | 5.10 | 5.12 | 0.09 | 0.13 | 0.23 |
| Sample 4 | 5.70 | 5.71 | 0.62 | 1.29 | 1.79 |

The degradation products of paclitaxel include: Baccatin III, Ethyl Ester Side Chain of Paclitaxel, 10-Deacetyl Paclitaxel, 10-Deacetyl-7-Epi-paclitaxel, and 7 Epi-paclitaxel.

As is evident from the above results, purification of cremophor results in reduction of the pH of cremophor from about

| Cation Content: | | | | | | | |
|---|---|---|---|---|---|---|---|
| Identity | Zinc | Magnesium | Sodium | Potassium | Aluminum | Tin | Calcium |
| Cremophor ELP (BASF) | 2.93 | 7.86 | 28.67 | 3.00 | 0.78 | 1.28 | 32.62 |
| ELP-Prep 1 | 2.10 | 5.99 | 31.39 | 3.36 | 0.33 | 0.78 | 22.25 |
| ELP-Prep 2 | 1.89 | 4.60 | 31.52 | 3.48 | 0.37 | 0.32 | 17.83 |
| ELP-Prep 3 | 1.58 | 4.60 | 32.12 | 3.39 | 0.13 | 0.33 | 18.89 |

All values are in ppm

As is evident from the above table there is substantial decrease in the concentrations of most of the cations listed above except sodium and potassium All the above tabulated cations are known to promote degradation of paclitaxel.

| Anion Content: | | | |
|---|---|---|---|
| Identity | Chloride | Bromide | Sulphate |
| Cremophor ELP (BASF) | 23.211 | 0.657 | 6.747 |
| ELP-Prep 1 | 4.625 | ND | 2.545 |
| ELP-Prep 2 | 14.673 | ND | 6.014 |
| ELP-Prep 3 | 15.386 | ND | 2.352 |

All values are in ppm;
ND = Not detectable

As is evident from the above table there is a decrease in the concentrations of the inorganic anions, as compared to the untreated Cremophor ELP from M/s BASF. These purified cremophor samples were then used to make formulations of 5.70 to around 5.10. As shown in Table 1—Samples 1 to 3 prepared with purified cremophor are much more stable in terms of degradation products of paclitaxel as.compared to sample –4. Thus, cremophor ELP purified using the process of the invention improves the stability of paclitaxel formulation significantly as compared to the formulation made using untreated Cremophor ELP.

The foregoing description of the preferred embodiment of the invention has been presented for purpose of illustration and description. It is not intended to be exhaustive or to limit the invention to precise parameters disclosed. Obvious modifications or variations are possible in light of the above teachings. The embodiment has been chosen and described to provide the best illustration of the principles of the invention and its practical applications to thereby enable one of the ordinary skill in the art to utilize the invention in various embodiments and with various modifications like using various size chromatographic columns, different types of reverse-phase chromatographic materials, column packing materials of different particle size, and/or different chromatographic temperatures etc. All such modifications and variations are within the scope of the invention as determined by the appended claims.

The invention claimed is:

1. A process for purifying a castor oil derivative, non-ionic solvent comprising the steps of:
   a) forming a solution of said solvent in alcohol and water, with or without aid of heating;
   b) loading the solution on to a chromatography column packed with reverse phase silica;
   c) running the chromatography column using de-ionized water as the mobile phase to purify the solvent;
   d) running the chromatography column using an eluent recovering the purified solvent; and
   e) evaporating the residual water and the eluent.

2. The process according to claim 1, wherein the solvent is polyethoxylated castor oil or polyoxyl-35-castor oil.

3. The process according to claim 1, wherein the solvent is polyehtoxylated castor oil.

4. The process according to claim 1, wherein the alcohol is selected from the group consisting of methanol, ethanol, butanol and isopropanol.

5. The process according to claim 1, wherein the alcohol is ethanol.

6. The process according to claim 1, wherein the eluent is selected from the group consisting of methanol, ethanol, isopropyl alcohol, acetone, acetonitrile and tetrahydrofuran.

7. The process according to claim 1, wherein the eluent is acetone.

8. The process according to claim 1, wherein the de-ionized water is HPLC grade.

9. The process according to claim 1, wherein in step (a) said solution is a solution of polyethoxylated castor oil, alcohol and water.

10. The process according to claim 1, wherein said step of forming said solution comprises mixing about polyethoxylated castor oil, dehydrated ethanol and de-ionized water in a ratio of 10:1:33 w/v/v with or without the aid of heat.

11. The process according to claim , wherein said step of forming said solution comprises mixing about 300 gm of polyethoxylated castor oil, 30 gm of dehydrated ethanol and one liter of HPLC grade non ionic water with or without the aid of heat.

12. The process according to claim 1, wherein said solvent is polyethoxylated castor oil and the step the chromatography column comprises a column of 15×30 cms packed with reverse phase silica of C-8 or C-18 type having a particle size of 30-60μ.

13. The process according to claim 1, wherein the step of running the chromatograph to purify the solvent comprises the use of de-ionized water as the mobile phase for 1 to 50 minutes.

14. The process according to claim 13, wherein the de-ionized water is HPLC grade.

15. The process according to claim 1, wherein the aqueous fractions are discarded.

16. A process for purifying a polyoxyl 35 castor oil solution said solution comprising polyoxyl 35 castor oil, water and an alcohol said process comprising loading the solution on to a chromatography column packed with reverse phase silica and running the chromatograph using de-ionized water as the mobile phase followed by eluting the purified polyoxyl 35 castor oil with methanol, ethanol or acetone evaporating the residual alcohol, water and methanol, ethanol or acetone to obtain purified polyoxyl 35 castor oil adapted to produce, when combined with paclitaxel, a pharmaceutical composition not showing more than 0.3% degradation products of paclitaxel identified as Baccatin III, Ethyl ester side chain of Paclitaxel, 10-Deacetyl paclitaxel, 10-Deacetyl 7-epipaclitaxel and 7-epipaclitaxel, after being stored at 50° C. for 10 days.

17. A process for purifying a polyoxyl 35 castor oil solution said solution comprising polyoxyl 35 castor oil, water and an alcohol said process comprising loading the solution on to a chromatography column packed with reverse phase silica of C-8 or C-18 type having a particle size of 30-60μ and running the chromatograph using de-ionized water (HPLC grade as the mobile phase followed by eluting the purified polyoxyl 35 castor oil with methanol, ethanol or acetone, evaporating the residual alcohol, water and methanol, ethanol or acetone to obtain purified polyoxyl 35 castor oil adapted to produce, when combined with paclitaxel, a pharmaceutical composition not showing more than 0.3% degradation products of paclitaxel identified as Baccatin III, Ethyl ester side chain of Paclitaxel, 10-Deacetyl paclitaxel, 10-Deacetyl 7-epipaclitaxel and 7-epipaclitaxel, after being stored at 50° C. for 10 days.

18. The process according to claim 17, wherein the eluent is acetone.

* * * * *

UNITED STATES PATENT AND TRADEMARK OFFICE
CERTIFICATE OF CORRECTION

| | | |
|---|---|---|
| PATENT NO. | : 7,699,987 B2 | Page 1 of 1 |
| APPLICATION NO. | : 11/449476 | |
| DATED | : April 20, 2010 | |
| INVENTOR(S) | : Anand C. Burman et al. | |

It is certified that error appears in the above-identified patent and that said Letters Patent is hereby corrected as shown below:

Title page, (73), Assignee:  "Dabur Pharma Ltd." should read
--Fresenius Kabi Oncology Ltd.--

Signed and Sealed this
Thirty-first Day of May, 2011

David J. Kappos
*Director of the United States Patent and Trademark Office*